US00PP21083P2

(12) United States Plant Patent
Hofmann

(10) Patent No.: US PP21,083 P2
(45) Date of Patent: Jun. 22, 2010

(54) **NEW GUINEA *IMPATIENS* PLANT NAMED 'FISNICS ORRED'**

(50) Latin Name: *Impatiens hawkeri*
Varietal Denomination: Fisnics Orred

(75) Inventor: Birgit Christa Hofmann, Ruedesheim (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/381,507

(22) Filed: Mar. 12, 2009

(51) Int. Cl.
*A01H 5/00* (2006.01)

(52) U.S. Cl. ..... Plt./318.3

(58) Field of Classification Search ..... Plt./318.3
See application file for complete search history.

*Primary Examiner*—Annette H Para

(74) *Attorney, Agent, or Firm*—S. Matthew Edwards

(57) ABSTRACT

A New Guinea *Impatiens* plant named 'Fisnics Orred,' particularly distinguished by the deep orange-red flower color, large, zygomorphic flowers well above the foliage, medium green foliage, relatively small and narrow leaves, compact during greenhouse cultivation, later becoming medium to tall, but not very wide, early flowering and rich flowering throughout the summer.

1 Drawing Sheet

Latin name of the genus and species of the plant claimed: *Impatiens hawkeri.*

Varietal denomination: 'Fisnics Orred'.

BACKGROUND OF THE NEW PLANT

The present invention comprises a New Guinea *Impatiens*, botanically known as *Impatiens hawkeri* and hereinafter referred to by the variety name 'Fisnics Orred'.

'Fisnics Orred' is a product of a planned breeding program. The new cultivar has large, orange-red flowers, medium green foliage, narrow leaves and about medium sized plant habit.

'Fisnics Orred' originated from a hybridization made in the summer of 2004 in a controlled breeding program in Hillscheid, Germany. The female parent was an unpatented hybrid seedling identified as 'K04-3516-6,' with red flowers having a small pink eye, and with compact plant habit.

The male parent of 'Fisnics Orred' was an unpatented hybrid seedling identified as 'K02-0172-1' with orange flower color in combination with dark green foliage and fairly tall plant habit.

'Fisnics Orred' was selected as one flowering plant within the progeny of the stated cross in the spring of 2005 in a controlled environment in Moncarapacho, Portugal.

The first act of asexual reproduction of 'Fisnics Orred' was accomplished when vegetative cuttings were taken from the initial selection in July 2005 in a controlled environment in Moncarapacho, Portugal.

Horticultural examination of plants grown from cuttings of the plant initiated in February 2006 in Hillscheid, Germany, and continuing thereafter, has demonstrated that the combination of characteristics as herein disclosed for 'Fisnics Orred' are firmly fixed and are retained through successive generations of asexual reproduction.

'Fisnics Orred' has not been observed under all possible environmental conditions. The phenotype may vary significantly with variations in environment such as temperature, light intensity and day length.

Plant Breeder's Rights for this cultivar were applied for in Canada on Apr. 29, 2008 and in Switzerland on Mar. 20, 2008. 'Fisnics Orred' has not been made publicly available more than one year prior to the filing of this application.

BRIEF DESCRIPTION OF DRAWING

The accompanying photographic drawing shows typical flower and foliage characteristics of 'Fisnics Orred' with colors being as true as possible with an illustration of this type.

The photographic drawing shows a flowering potted plant of the new variety.

DETAILED BOTANICAL DESCRIPTION

The measurements were taken in Hillscheid, Germany, in late August 2008 on plants that were growing outdoors. Culture of these plants had started in late February 2008 when rooted cuttings were planted into 12 cm pots, placed in the greenhouse and cultivated at a minimum temperature of 16° C. In late May plants were transplanted, 3 each, into 45 cm diameter containers that were placed outdoors, two containers per variety were placed along the greenhouse under light rain protection.

Color Chart used: Royal Horticultural Society Colour Chart (R.H.S.) 2001

BRIEF SUMMARY OF INVENTION

The following observations, measurements, and comparisons describe plants grown indoors and outdoors in Hillscheid, Germany, and Chatelerault, France. The following traits have been repeatedly observed and are determined to be basic characteristics of the new variety. The combination of these characteristics distinguishes this New Guinea *Impatiens* as a new and distinct variety.

1. Brilliant, deep orange-red flower color.
2. Large flowers, somewhat zygomorphic, borne well above the foliage.

3. Medium green foliage, with relatively small and narrow leaves.
4. Medium to strong vigor.
5. Well-branched, mounding plant habit.
6. Early flowering and continuously and rich flowering.

DIFFERENCES BETWEEN THE NEW VARIETY 'FISNICS ORRED' AND SIMILAR VARIETIES

In comparison to 'Fisnics Scarlet,' U.S. Plant Pat. No. 14,672, 'Fisnics Orred' has somewhat deeper green foliage color, and somewhat taller plant habit.

In comparison to Paradise 'Timor' (commercial name) Plant Breeder's Rights protected as 'Kitim,' 'Fisnics Orred' has larger and less cup-shaped flowers, and generally taller and more upright plant habit.

In comparison to 'Fisnics Orga,' U.S. patent application Ser. No. 12/077,382, 'Fisnics Orred' has a deeper, orange-red hue of flower color, somewhat less deep green foliage color, narrower leaf shape, and possibly slightly taller plant habit, as plants develop less wide, but more upright.

Plant:

*Form, growth and habit.*—Well-branching, initially relatively compact, during the summer mounding and medium to tall in height.
*Plant height.*—32 cm.
*Plant width.*—35–40 cm.
*Number of branches.*—About 20.
*Time to produce a finished flowering plant.*—9–10 weeks for a 12 cm pot.
*Time to initiate and develop roots.*—18 days or less at 22° C.

Stem:

*Color of stem.*—Green, RHS 146C or brownish, RHS 180A, partly mingled.
*Length of stem.*—24–29 cm.
*Diameter.*—0.8–0.9 cm.
*Length of internodes.*—5.5–8 cm.
*Texture.*—Smooth, glabrous.

Foliage:

*Arrangement.*—Mainly in whorls.
*Immature leaf color, upper surface.*—Partly grass-green (lighter than the mature leaves), RHS 137D to 144A.
*Immature leaf, lower surface.*—RHS 138B.
*Mature, leaf color, upper surface.*—Medium green, RHS 137B to 137C.
*Mature leaf, lower surface.*—RHS 138B.
*Length.*—Mostly 10.5–11.5 cm.
*Width.*—3.0–3.8 cm.
*Shape.*—Elliptical, relatively narrow.
*Base shape.*—Acute.
*Apex shape.*—Acute to acuminate.
*Margin.*—Slightly serrate, ciliate.
*Texture.*—Smooth, slightly glossy.
*Color of veins, upper surface.*—Near base light pink, RHS 51D to 145B, light green towards tip.
*Color of veins, lower surface.*—Light green, RHS 146D near base, fading towards tips.

Petiole:

*Color upper surface.*—Pink, RHS 51C or nearly white, RHS 150D.
*Color lower surface.*—Light green, RHS 145C.
*Length.*—1.0–2.0 cm.
*Diameter.*—3 mm.
*Texture.*—Nearly glabrous.

Inflorescence:

*Start of flowering.*—Approximately 9 weeks after planting of rooted cuttings.
*Blooming habit, duration of flowering.*—Continuous flowering from spring through fall, in the greenhouse year round, depending on light intensity.
*Type of inflorescence.*—Flowers appear solitary in the leaf axils of the upper stem nodes.
*Number of flowers and buds per node.*—About 6–8, in various stages of development.
*Number of flowers per plant.*—25–30.
*Lastingness of individual blooms.*—Approximately 9–12 days (18° C., greenhouse in springtime).

Pedicel:

*Color of pedicel.*—Light green, RHS 145C, to cream, RHS 158A, to light brown, RHS 179C.
*Length of pedicel.*—6.0–6.5 cm.
*Diameter of pedicel.*—1 mm.
*Texture.*—Flexible, glabrous.

Flower:

*Form.*—Single-type, 5 petals.
*Shape of corolla.*—Large, zygomorphic, with overlapping petals, a little butterfly-shaped at times with the lateral petals slanting upwards.
*Overall color.*—Brilliant orange-red.
*Upper surface.*—RHS 44B, uniform.
*Markings.*—Very weak: pink colored eye zone, RHS 51A.
*Lower surface.*—RHS 40A, or intermediate betw. 40A and 40B.
*Length diameter of flower.*—Up to 8.5 cm.
*Width of flower.*—7.5–8.0 cm.
*Depth.*—1.0–1.5 cm.

Petals:

*Shape.*—Banner petal: cordate, lateral and lower petals obovate.
*Apex shape.*—Emarginate.
*Base.*—Attenuate.
*Margin.*—Entire.
*Upper (banner) petal, length.*—3.9–4.1 cm.
*Upper petal, width.*—5.4–6.0 cm.
*Lateral petals, length.*—3.6—3.8 cm.
*Lateral petals, width.*—4.0 cm.
*Lower petals, length.*—3.9–4.2 cm.
*Lower petals, width.*—4.7–4.8 cm.
*Petal texture.*—Smooth, silky.

Spur:

*Shape.*—Downward directed, elongate.
*Color.*—Reddish, RHS 53D.
*Length.*—6.0 cm.
*Diameter.*—3 mm.

Bud (just before opening):

*Shape.*—Ovoid.
*Length.*—2.1 cm.
*Diameter.*—1.5 cm.
*Color.*—Orange-red, RHS 43A.

Calyx:

*Form, shape.*—4–5 sepals, the upper one fused, crest-like, with the underside of the banner petal, 2 lateral sepals, and a large sepal (2 fused sepals) bearing the spur.
*Color of lateral sepals.*—Light green, RHS 145B or 146D to reddish, RHS 47C.
*Color of lower sepals.*—Pink, RHS 51C and lighter in parts.

*Length of lateral sepals.*—1.5–1.8 cm.
*Width of lateral sepals.*—0.7 cm.
*Length of lower sepals.*—1.8–2.0 cm.
*Width of lower sepals.*—1.2–1.4 cm.
*Sepal shape.*—Ovate.
*Apex shape.*—Acute to cuspidate.
*Base shape.*—Rounded.
*Margins.*—Entire.

Reproductive organs:

*Gynoecium.*—
*Pistil.*—One.
*Length.*—6 mm.
*Ovary shape.*—Elongate, 5-celled.
*Color of ovary.*—Green, RHS 144A.
*Style and stigma.*—Very short, RHS 13D in color.
*Androeceum.*—5 stamen, fused, the anthers hooded.
*Diameter of androeceum.*—6–7 mm.
*Surface color.*—Orange, RHS 43A or 44B.
*Pollen amount.*—Moderate.
*Color of pollen.*—Whitish yellow, RHS 8D.
*Fertility/seed set.*—No seed set observed.

Disease/pest resistance: Disease resistance or susceptibility has not been observed on this hybrid.

What is claimed is:

1. A new and distinct variety of New Guinea *Impatiens* plant named 'Fisnics Orred,' substantially as illustrated and described herein.

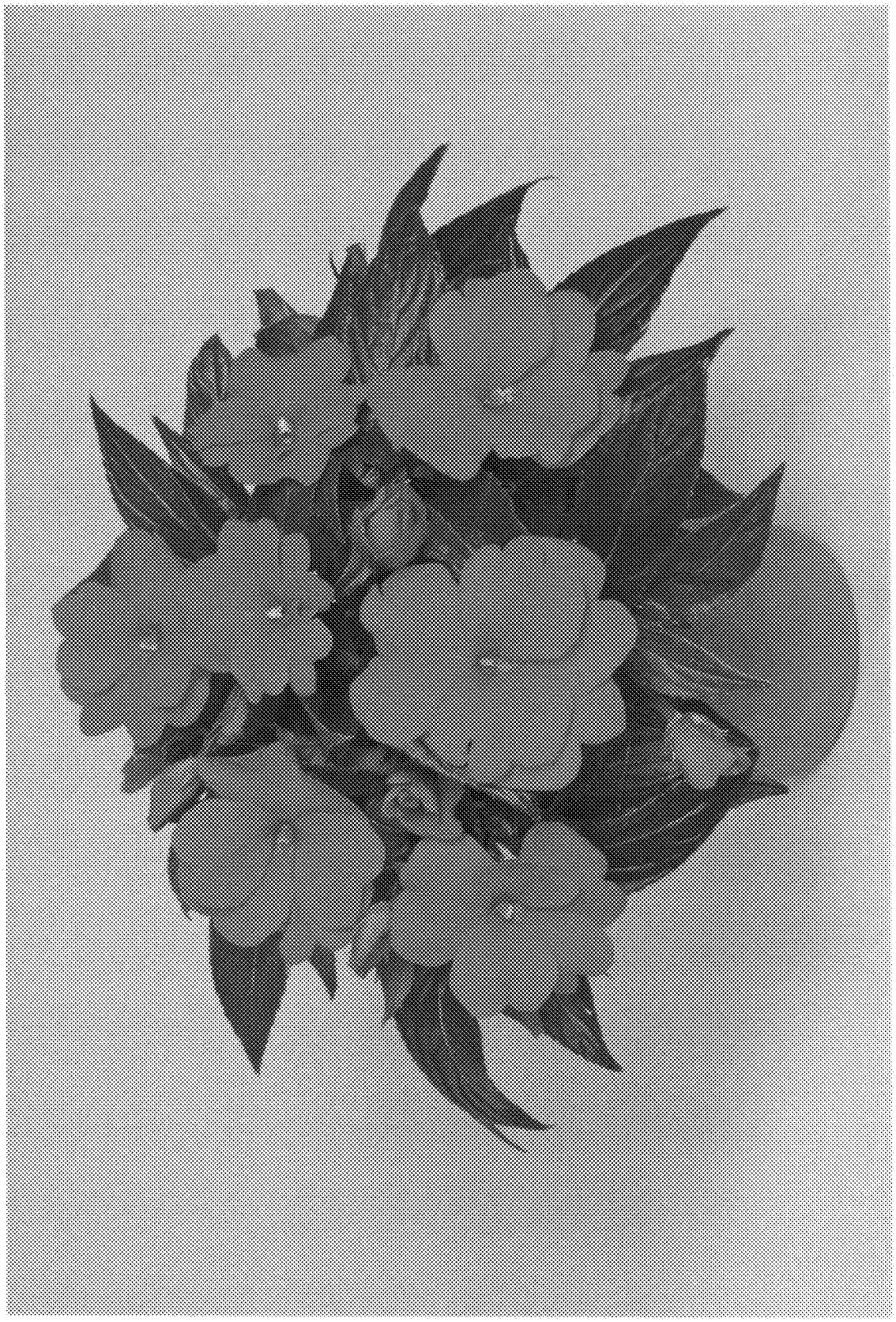

* * * * *